United States Patent [19]
Herzberg

[11] Patent Number: 5,078,483
[45] Date of Patent: Jan. 7, 1992

[54] DISPOSABLE TUBULAR FILM COVER FOR ARTHROSCOPY CAMERAS AND METHOD FOR COVERING ARTHROSCOPY CAMERAS BY MEANS OF SUCH A DISPOSABLE COVER

[75] Inventor: Wolfgang Herzberg, Wedel, Fed. Rep. of Germany

[73] Assignees: Renate Dunsch-Herzberg, Wedel; Gudrun Voss, Hamburg, both of Fed. Rep. of Germany

[21] Appl. No.: 302,314

[22] Filed: Jan. 25, 1989

[30] Foreign Application Priority Data
Sep. 23, 1988 [DE] Fed. Rep. of Germany ... 8812027[U]
Dec. 15, 1988 [DE] Fed. Rep. of Germany ... 8815549[U]

[51] Int. Cl.⁵ .................... B65D 85/38; G02B 27/00
[52] U.S. Cl. .................... 359/510; 359/900; 359/511
[58] Field of Search ............... 350/319, 320, 579–580, 350/585–589, 321, 582–587; 128/1 R, 4–8, 849–856, 877, 206.12–206.25; 354/62

[56] References Cited

U.S. PATENT DOCUMENTS

| | | | |
|---|---|---|---|
| 3,698,791 | 10/1972 | Walchle et al. | 350/587 |
| 4,045,118 | 8/1977 | Goraci | 350/585 |
| 4,522,196 | 6/1985 | Cunningham et al. | 350/587 |
| 4,561,540 | 12/1985 | Hunter et al. | 350/585 |
| 4,649,910 | 3/1987 | Poenitsch | 128/165 |
| 4,799,779 | 1/1989 | Mesmer | 350/585 |

FOREIGN PATENT DOCUMENTS

| | | |
|---|---|---|
| 8711189 | 12/1987 | Fed. Rep. of Germany . |
| 1418637 | 8/1988 | U.S.S.R. ............ 350/587 |

*Primary Examiner*—Bruce Y. Arnold
*Assistant Examiner*—Thong Neuyen

[57] ABSTRACT

A sterile disposable arthroscopy camera cover made from tubular film folded onto itself and forming a package including a plurality of folded layers of film. One end portion of the tubular film extends into and through the other end portion of the tubular film and in the direction of the other end so that the two tubular film ends are located at the same side of the film package. The folded layers which comprise the package may extend in the direction of the tubular film axis or transversely of the axis.

14 Claims, 6 Drawing Sheets

Fig.1

Fig.2

DISPOSABLE TUBULAR FILM COVER FOR ARTHROSCOPY CAMERAS AND METHOD FOR COVERING ARTHROSCOPY CAMERAS BY MEANS OF SUCH A DISPOSABLE COVER

BACKGROUND OF THE INVENTION

The present invention relates to a disposable cover fabricated from a tubular film for arthroscopic cameras and a method for covering arthroscopic cameras by means of such a disposable cover.

Due to the introduction of video cameras into the technique of arthroscopy, the necessity has arisen for making a non-sterile camera fitted with cables available to the surgeon by means of a sterile film cover. In the first generation of such covers, simply folded tubular films of polyethylene were available which were pushed over the camera in a relatively laborious fashion. In the second generation, these covers were developed with a so-called "insertion folding", that is to say the tubular film was drawn in a telescopical manner and could thus be simply drawn over the camera.

Both the "simply" folded as well as the "insertedly" folded tubular films require adhesive tapes for sealing the tube ends.

Since the "sterile" end of the tube may possibly be exposed to a considerable degree of humidification the risk of the adhesive tape becoming detached exists,
  The exceedingly cramped arrangement of supplying and down-leading cable connections at the sterile end of the tube does not permit the application of a broad adhesive tape.
  Added to which is the circumstance that the known tubular films are, at their sterile ends, provided with a tapering which is produced by two welded, converging separations. These two welds are located within the area most stressed by handling and constitute a serious danger zone as regards the violation of the sterility. However, dispensing with these welds would result in the closure effected with the aid of the adhesive tape producing a certain "candy bag" effect with an interfering brim formation.

The present invention solves the technical problem of providing a disposable cover fabricated from tubular film for rapidly and safely covering arthroscopic cameras, whereby increased safety within the problem zone is achieved and no weak points due to welds will arise while, at maintenance of same time, the sterility is improved.

SUMMARY OF THE INVENTION

In a thusly constructed disposable cover, welds, perforations and adhesive tapes are dispensed with at the tube end on the arthroscope side since tube clamps are employed which, in their handling, are safer and more accurate as compared to adhesive tapes and, in addition, completely resistant to humidity as well. The disposable cover is simple and speedy to handle. A double security is provided by the twofold film layer within the problem zone. The closure is moisture-proof and the sterility is not jeopardized by any welds. The fixation of the cable is more comfortable both in the operating field as well as on the monitor.

One construction which is particularly advantageous in which the package of folded layers is accommodated in a container so as to form a tubular film supply. A disposable cover fabricated from a tubular film constructed in such a manner renders possible the accommodation of a concertina-like folded tubular film inside a disk-shaped container with perforations in the oppositely located container walls so that it is possible to pull the two ends of the specially folded tubular film out of the interior of the container in order to be able to introduce the arthroscope through the container into the inner space of one of the tubular film sections. In this connection the tubular film is arranged in such a way that the tubular film folding comes to be located within the interior of the container, while one end of the tubular film can be drawn over the other end, to be more specific, in the parallel direction to the tubular film, in which process tubular film material is removed from the tubular film folding. If an arthroscope is passed through the interior of the tubular film receiving container and introduced into the internal tubular film section, in that case, within the area of the arthroscope, the tying off of the tubular film is effected with the aid of a tubing clamp, whereupon the outer terminal section of the tubular film is drawn over the internally located tubular film so that, after the complete unfolding of the tubular film, the empty container remains, whereas the camera is then enveloped twice in film.

Owing to the construction according to the invention, the use of a disposable cover fabricated from a tubular film is possible which is devoid of weak points due to welds. The cover ensures that the sterility endangered by manipulation at the sterile end is doubly protected. In its handling, the cover corresponds to the handling comfort of the known insertion folding. At its sterile end, the cover is provided with an absolutely moisture-proof closure. The cramped conditions at the sterile end of the cover are not annoyingly overtaxed by a space-saving closure. Both in the tubing center as well as at the non-sterile end, a secure attachment and a secure closing are possible. By the folded section of the tubular film being disposed within the interior of the container, a secure storage and an easy handling of the tubular film is ensured together with a high degree of sterility.

According to the invention, the method for covering arthroscopy cameras with a disposable cover consists in that the free end of the externally located section of a sterile tubular film folded together so as to form a package of folded layers with the folded layers extending parallelly to the longitudinal direction of the tubular film is pulled off by one section from the package of folded layers and is drawn across over the internally located section of the tubular film which has been pulled slightly out of the package of folded layers, is hereupon inserted into the inner space of the internally located section of the tubular film of the arthroscope, the tubular film is, within the area of the free tubular film end, tied off behind the optical system of the arthroscope, thereafter the externally located section of the tubular film supply of the package of folded-layers is drawn over the camera mounted on the optical system of the arthroscope, until the internally located tubular film section, within the tying-off area, is tucked inside out around the optical system of the arthroscope so as to form a two-layer film cover and the free end of the pulled-off tubular film is tied off behind the camera. After this is done, a tubular film supply is used which consists of numerous layers of folds formed from the tubular film which extend in parallel relation to the longitudinal direction of the tubular film.

Further, and in accordance with the invention, a method is provided for covering an arthroscopy camera which includes the steps of providing a sterile cover fabricated from tubular film, folding successive contiguous sections of the tubular film onto each other to define a film supply including multiply package of folded layers having two end sections defining the open terminal ends of the tubular film, moving the end sections relative to each other to extend one of the end sections through and outwardly beyond the terminal end of the other of the end sections and position the terminal end of the said one end section in outwardly spaced relation to the terminal end of the other end section, inserting an arthroscope into the one end section in the direction of the terminal end thereof, tying off the one end section within the region of the optical system of the arthroscope and in inwardly spaced relation to the terminal end of the one end section, inserting the camera into the one end section through the open terminal end thereof to dispose the camera within the one end section, mounting the camera on the optical system of the arthroscope and within the one end section, pulling the other end section outwardly over the one end section and outwardly beyond the terminal end of the one end section to unfold the multiply film package and turn the portion of the tubular film adjacent the tied off part of the one end section inside out around the optical system of the arthroscope to enveloping the one end section and form a two layer film cover for the camera, and tying off the other end section outwardly of the camera.

BRIEF DESCRIPTION OF THE DRAWINGS

Embodiments of the invention are explained below with the aid of the drawings. Thus

DETAILED DESCRIPTION OF THE PREFERRED EMBODIMENT

Figure 1:
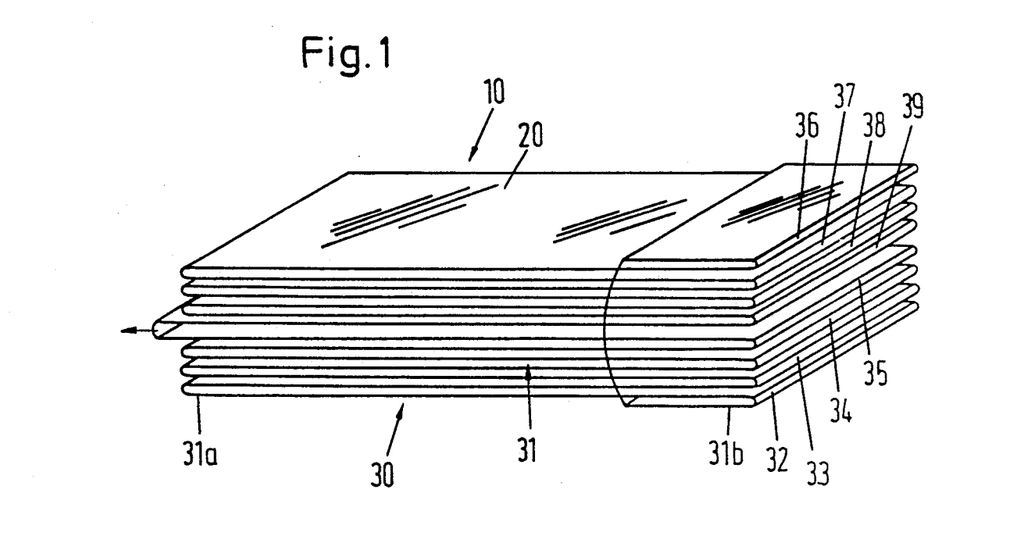
FIG. 1 shows, in a diagrammatical view, a disposable cover with a supply of stored tubular film from a package of folded layers comprising a plurality of folded layers extending parallel relation to the longitudinal direction of the tubular film.

According to the FIG. 1, the disposable cover 10 for arthroscopy cameras consists of a tubular film 20 and is provided with a supply of tubular film 30 formed from the tubular film 20, which supply comprises a plurality of folded layers 32, 33, 34, 35, 36, 37, 38, 39 of the tubular film 20, which are combined into a package of folded layers 31, the terminal areas of which are identified with 31a, 31b.

Figure 4:
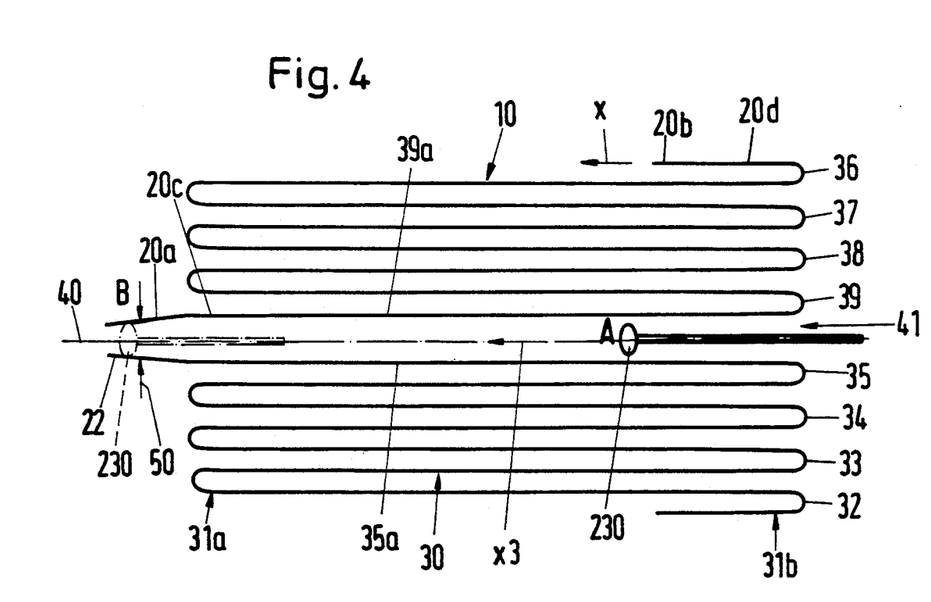
FIG. 4 shows a side elevation of the disposable cover according to the FIG. 1 during the insertion of the arthroscope.

In this disposable cover 10, the folded layers 32 thru 39 extend in parallel relation to the longitudinal direction of the tubular film which, in the FIG. 4, is indentified at 40. In the embodiment shown in the FIG. 1, the package of folded layers 31 is provided with eight folded layers 32 thru 39 made up from contiguous sections of the the tubular film 20, it being possible in this case for the number of folded layers to be smaller or larger. The folding of the tubular film 20 into the package of folded layers 31 is effected in the so-called insertion folding manner, which makes it possible that, when the free ends of the two external folded layers 32, 36 are pulled of in the direction of the arrow X by breaking up the folded layers, the entire tubular film 20 can be pulled off. The two ends of the tubular film 20 are indentified at 20a, 20b, in which connection 20a designates the tubular film end of the internal tubular film end section 20c, while 20b is the tube film end of the external tubular film end section 20d (FIG. 4).

Between the two internal folded layers 35, 39, an insertion opening 41 for an arthroscope 30 is formed, said insertion opening 41 being delimited by the two oppositely located tubular film sections 35a, 39a of the folded layers 35, 39, as a result of which these film sections 35a, 39a, form the internal tubular film section 20c.

This internal tubular film section 20c is passed out of the package of folded layers 31, to be more specific, out of its its terminal area 31a, and this by the formation of a projecting section 22 (FIG. 4).

In the outwardly FIG. 4, a tube clamp constructed in a manner known per se is indicated with 50, which will be dealt with in detail in the following.

Figure 3:
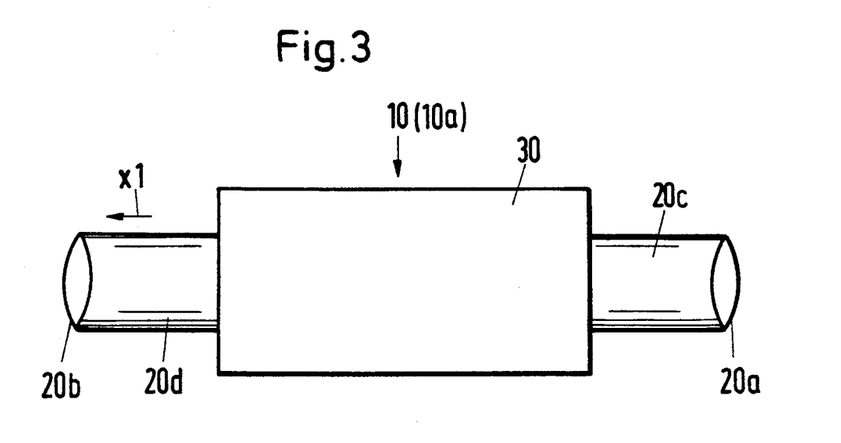
FIG. 3 shows a side elevation of the disposable cover with the tubular film storage container.

The FIG. 3 shows the tubular film 20 of the disposable cover with the tubular film supply 30 which comprises the folded layers 32 thru 39. For the utilization of the disposable cover 10 and for the development of a two-fold layer of film within the covering area of the arhtroscope and the camer necessary for this purpose, either the tubular film section 20d with its tubular film end 20b is drawn in the direction of the arrow X1 over the tubular film end 20c, or is passed and pulled to such an extent through the inner space of the tubular film section 20c that, in the final stage, the projecting tubular film section 22 is formed.

Figure 2:
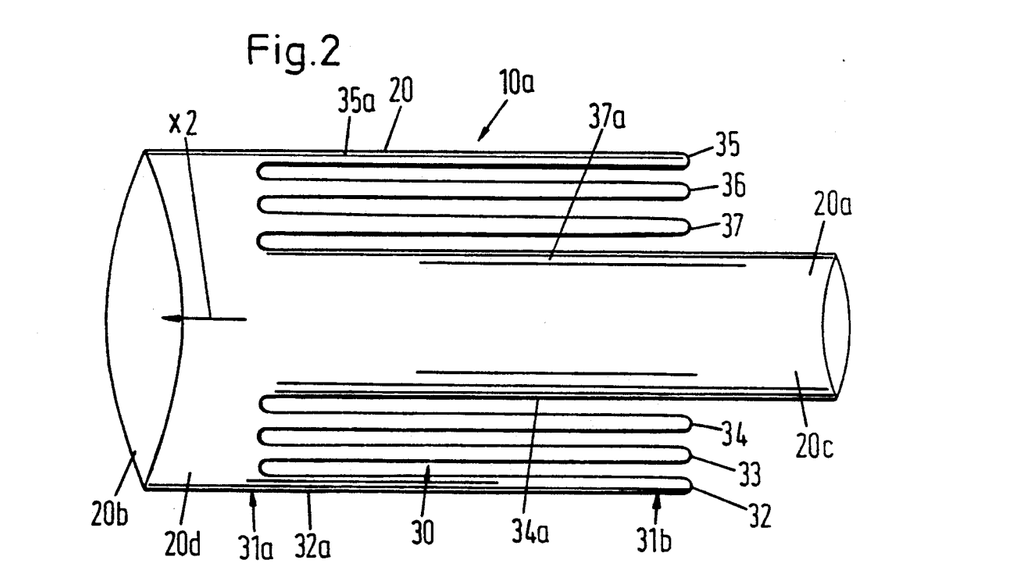
FIG. 2 shows a side elevation of a further embodiment of the disposable cover with folded layers extending in a different pattern.

In the disposable cover 10a according to the FIG. 2, the tubular film 20 is, in comparison with the folded layer in the disposable cover 10 as per FIG. 1, arranged in a different fashion. This disposable cover 10a is likewise provided with a tubular film supply 30 which is formed by the folded layers 32, 33, 34, 35, 36, 37, which constitute the package of folded layers 31. In this disposable cover 10a, the extended folded layers 34, 37 form, with their extended sections 34a, 37a, the wall areas or the circumferentially extending wall area of the internal tubular film section 20c, while the external tubular film section 20d is formed by the external film sections 32a, 35a of the folded layers 32, 35. Even when the tubular film ends 20a, 20b are located within the two terminal areas 31a, 31b of the package of folded layers 31, then, for the utilization of the disposable cover 10a, the internal tubular film section 20c is nevertheless pulled out in the direction of the arrow X2 from the end 20b of the external tubular film section 20d to such an extent that the projecting section 22 is formed. Also in the case of the disposable cover 10a, the supply of tubular film 30 is made up of a plurality of folded layers after the fashion of the insertion folding. Both in the disposable cover 10 as well as in the disposable cover 10a, the number of the folded layers can vary and will in each case depend on the length of the tubular film 20 employed which, in the end, also depends on the length of each folded layer. The package of folded layers 31 of the disposable cover 10, 10a may, for example, have four or even more folded layers 32 thru 39 or 32 thru 35, respectively.

Figure 5:
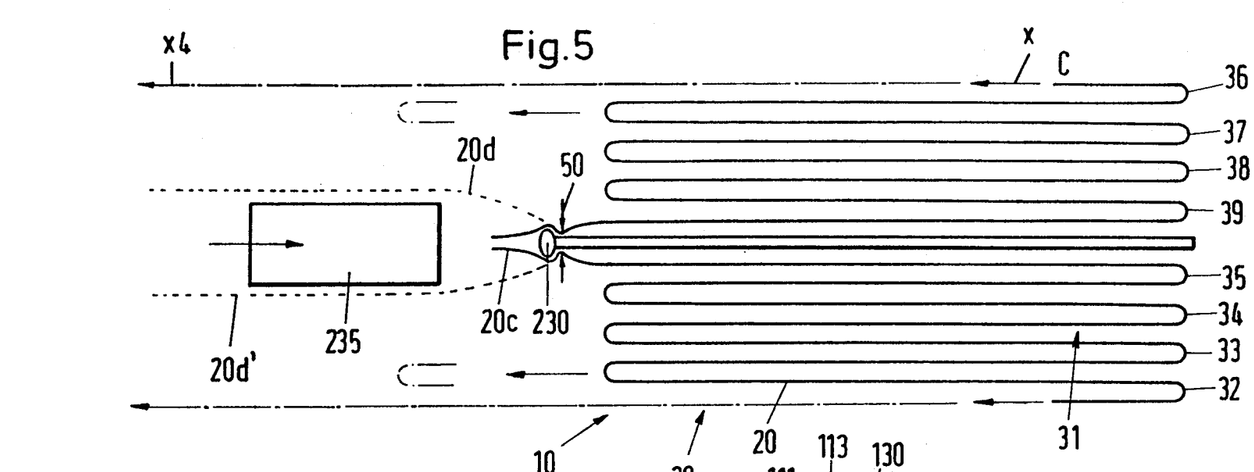
FIG. 5 shows a side elevation of the disposable cover according to FIG. 1 during the pulling-off phase of the tubular film.

The disposable cover 10 is employed as detailed below:

The arthroscope 230 is introduced into the insertion opening 41 between the two folded layers 35, 39 in the direction of the arrow X3 and comes to be located within the inner space of the internal tubular film section 20c as shown in FIG. 4. When, during the insertion, the arthroscope 230 has, from the position A and assumed the position B the internal tubular film section 20c is sealed behind the optical system of the arthroscope by means of a tube clamp 50, so that the arthroscope 230 is one-sidedly enveloped. Thereafter, the external tubular film section 20d is pulled off in the direction of the arrow X from the position C (FIG. 5) and is drawn over the camera 235 which is effected in the direction of the arrow X4. If the entire tubular film 20 is pulled off from the supply of tubular film 30 and consequently all the folded layers are used up, then the internal tubular film section 20c tucks itself inside out around the arthroscope 230, as indicated at 20d' (FIG. 5). In this way, both the arthroscope 230 as well as the camera 235, are covered by a double layer of film.

In the same manner in which the disposable cover 10 is handled, the disposable cover 10a is also employed.

Figure 6:
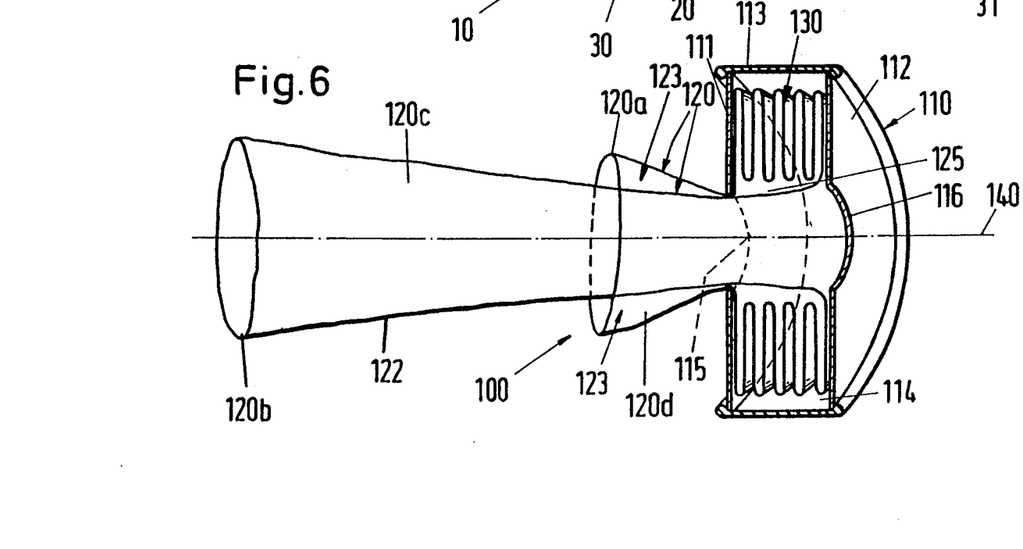
FIG. 6 shows, partly in a vertical section, a disposable cover with a supply of tubular film arranged in its container and comprising a package of several folded layers extending transversally to the longitudinal direction of the tubular film.
Figure 7:
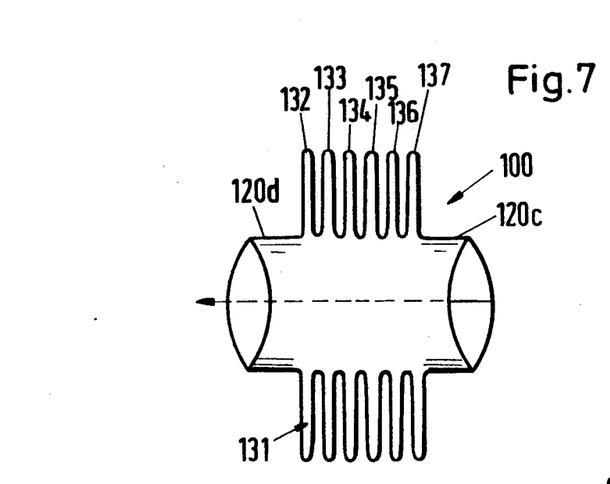
FIG. 7 shows a side elevation of the folding or gathering of the tubular film of the disposable cover according to FIG. 6.

According to the FIG. 6, the disposable cover identified with 100 likewise comprises a tubular film 120, in which case this disposable cover, too, is provided with a supply of tubular film 130 which is made up of a package of folded layers 132, 133, 134, 135, 136, 137, in which, as compared the arrangement of the disposable cover 10 or 10a, respectively, the folded layers 132 thru 137 extend transversally to the longitudinal direction identified with 140 in the FIG. 6, whereas the folded layers 32 thru 39 of the disposable cover 10 or 10a, respectively, extend in parallel relation to the longitudinal direction of the tubular film 40 (FIG. 7). In the case of the disposable cover 100, the folded layers 132 thru 137 are formed by gathering, while here, too, six folded layers are not mandatory either. The concertina-like folding is indicated with 121.

In the disposable cover 100, (FIG. 6) the supply of tubular film 130 formed by the folded layers 132 thru 137 is disposed within a container 110 in such a fashion that an internal tubular film section 120c and an external tubular film section 120d are formed. The terminal ends of the two film end sections are indicated with 120a, 120b: The internal tubular film section 120c is, prior to the employment of the disposable cover 100, constructed so as to be extended in comparison with the external tubular film section 120d, with the result that the extended section 122 of the internal tubular film section 120c projects from the tubular film end 120a of the external tubular film section 120. The shorter tubular film section and thus the external tubular film section 120d, is indicated at 123.

The tubular films 20, 120 of the disposable covers 10, 10a and 100 consist, for instance, of polyethylene or some other suitable plastic material. Provided that they can be sterilized, it will also be possible to use papers coated with plastic.

Figure 8:
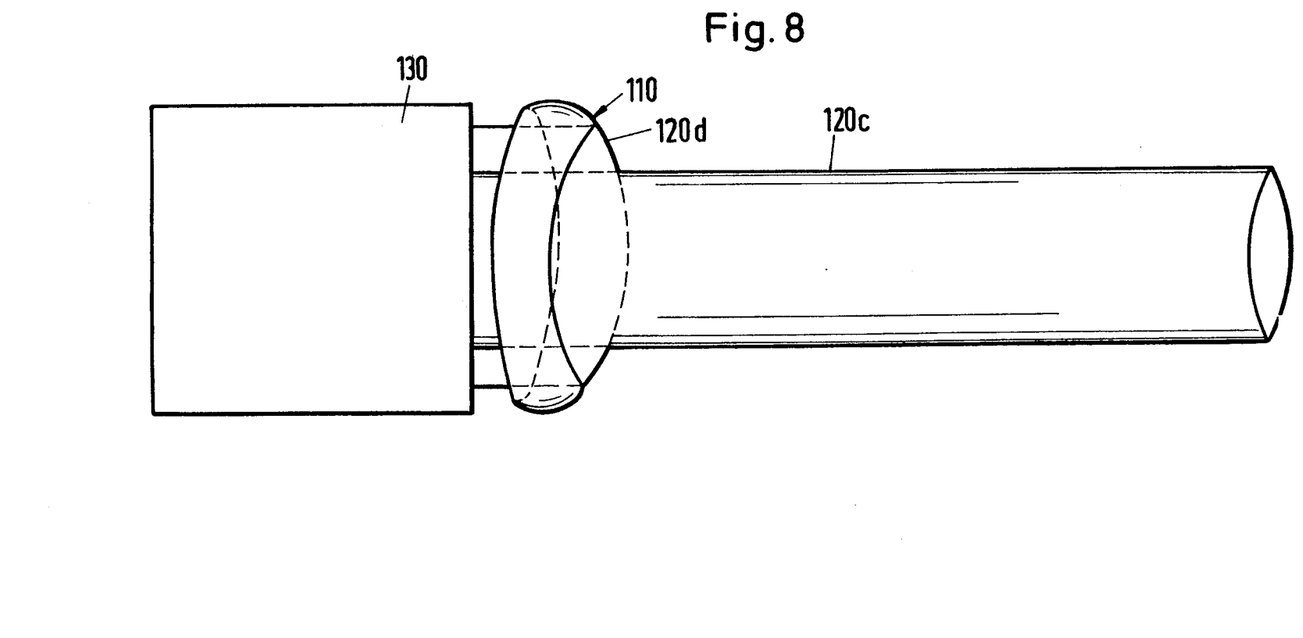
FIG. 8 shows a side elevation of the disposable cover according to the FIG. 6 with a tubular film storage container.

The storage container 110 (FIGS. 6-8) which houses the supply of tubular film 130 is constructed in a disk-like fashion and consists of two oppositely arranged walls with a circular area and of a wall 113 extending along the circumference of the two walls 111, 112, so that the container interior 114 is constituted of the three walls 111, 112 and 113.

Each wall 111 or 112 of the container 110 is provided with a central aperture 115 or 116. The two perforations or openings 115, 116 are coaxially aligned or congruent. The diameter of the perforations 115, 116 is smaller than the diameter of the tubular film 120. The perforations 115, 116 are preferably circular in configuration.

The tubular film 120 is, as appears from the FIG. 6, provided with a folding which is formed by the folded layers 132 thru 137. This supply of tubular film 130 with its folded layers 132 thru 137 is located within the interior 114 of the container 110. In this case, the arrangement of the folded layers 132 thru 137, or the pattern of the folding and also the disposition of the tubular film 120 are such that the end of the package of folded layers 131 which faces the wall 112 is passed through the inner space 125 formed by the folded layers 132 thru 137 and via the perforation 115 in the container wall 111 of the container 110 and pulled out to such an extent that a long, internal tubular film section 120c is obtained.

Figure 9:
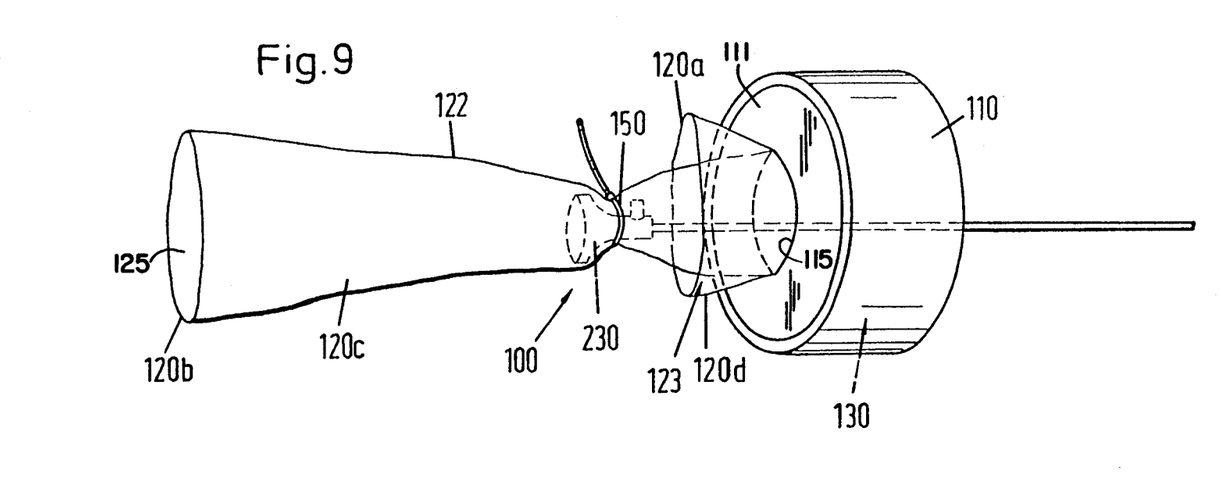
FIG. 9 shows, in a diagrammatical view, the disposable cover with the supply of tubular film disposed within a storage container with an arthroscope inserted into the internal tube section of the tubular film.

The end 120a of the tubular film 120 which faces the wall 111 of the container 110 is passed out of the perforation 115 and lies with a short section 120d around the longer, internal tubular film section 120c of the tubular film 120 (FIG. 9). In this fashion, the tubular film 120 overlaps with its end 120a of the shorter tubular film section 123 the internal tubular film section 120c, which thus lies within the inner space of the external tubular film section 120d. The opening located within the area of the tubular film end 120a of the external tubular film section 120d is identified with 127. The inner space of the longer, internal tubular film section 120c is indicated with 125 (FIGS. 6 and 9).

In the FIG. 9, the arthroscope 230 is indicated onto which the camera 235 can be mounted. 150 identifies a tube clamp that corresponds to the tube clamp 50 of the disposable cover 10 or 10a.

Prior to use, the sterilized disposable cover, i.e. the tubular film 120, lies within the container 110, the entire unit having been sterilized and packaged in a sterile fashion, which also applies to the disposable cover 10 or 10a. In this case, two tubular film ends 120a, 120b project from the perforation 115 in the wall 111 of the container 110 merely by the length of a gripping section. When using the disposable cover 100, the free end 120d of the tubular film section 120c is seized to begin with and pulled out from the container 110 until this tubular film section 120c has the approximate length shown in the FIGS. 6, 9 and 10. The other tubular film end 120a of the external tubular film section 120d is only pulled out from the interior 114 of the container 110 to a minor extent (FIG. 6).

The arthroscope is then passed through the perforations 115, 116 in the walls 111, 112 of the container 110, in the process the arthroscope 230 then comes to lie within the inner space of the internal, long tubular film section 120c. As depicted in the FIG. 9, the tubular film 120 is subsequently sealed within the area of the arthroscope 130 by means of the tube clamp 150.

Figure 10:
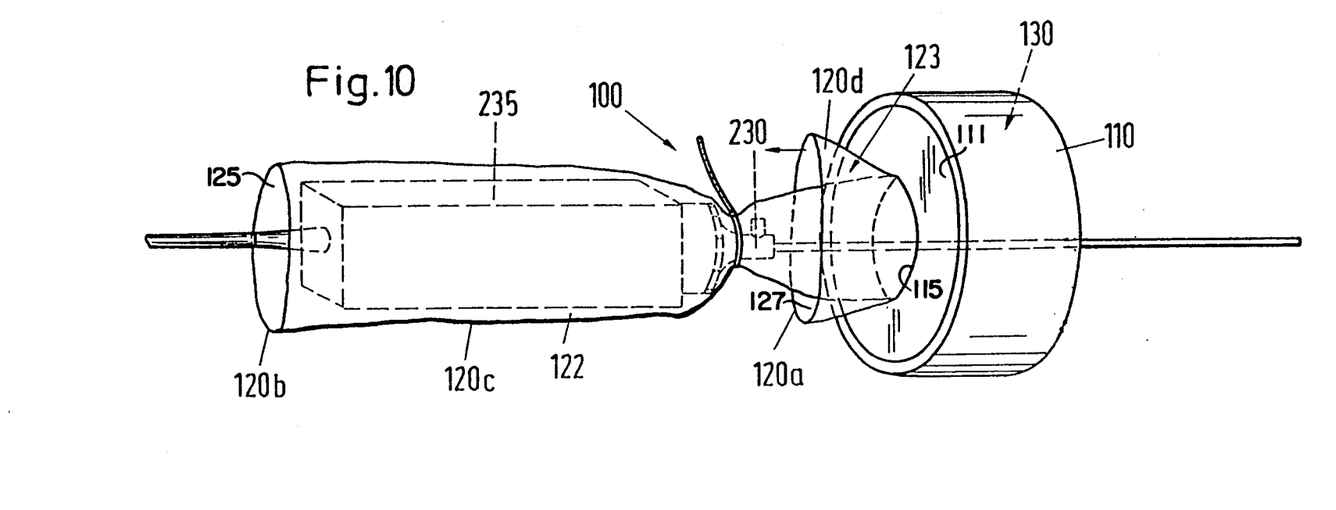
FIG. 10 shows, in a diagrammatical view, the disposable cover with the supply of tubular film disposed inside a storage container with the camera inserted into the internal tube section of the tubular film and mounted onto the arthroscope.

The camera 235 is hereupon inserted into the inner space 125 of the longer, internal tubular film section 120c and mounted onto the arthroscope 230 (FIG. 10). Further tube clamps are additionally employed in this case which seal both the sterile end of the tubular film 120 (FIG. 9) as well as the non-sterile end of the tubular film 120 and which, in addition, in the tube center, secure the cable encased in tubular film within the operating field.

Figure 11:
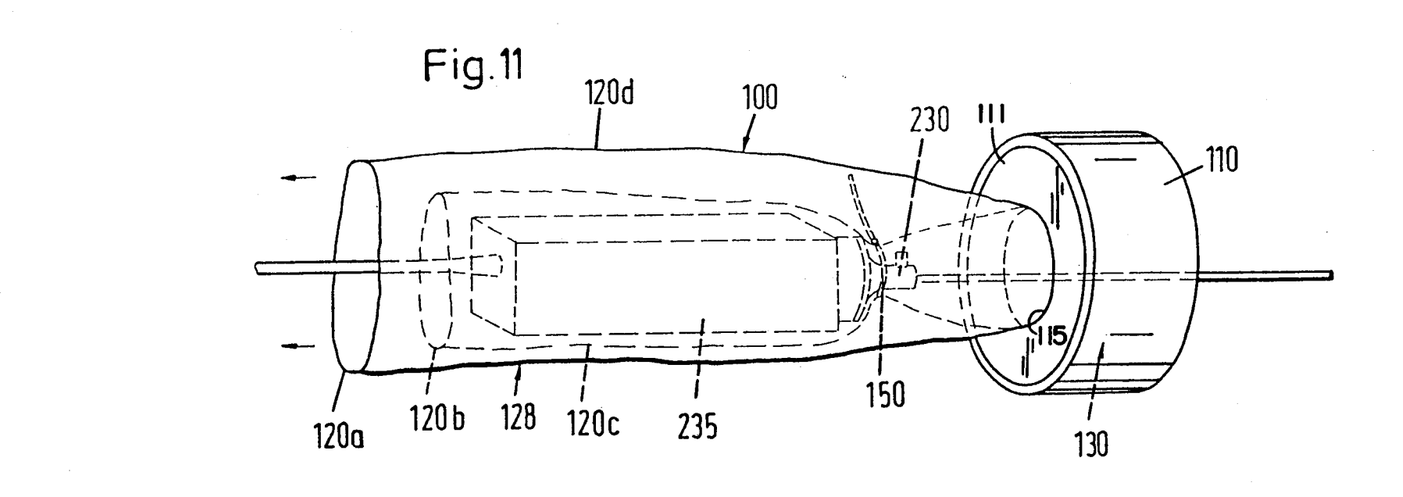
FIG. 11 shows, in a diagrammatical view, the disposable cover with the supply of tubular film disposed within a storage container with the camera doubly enveloped in tubular film.
Figure 12:
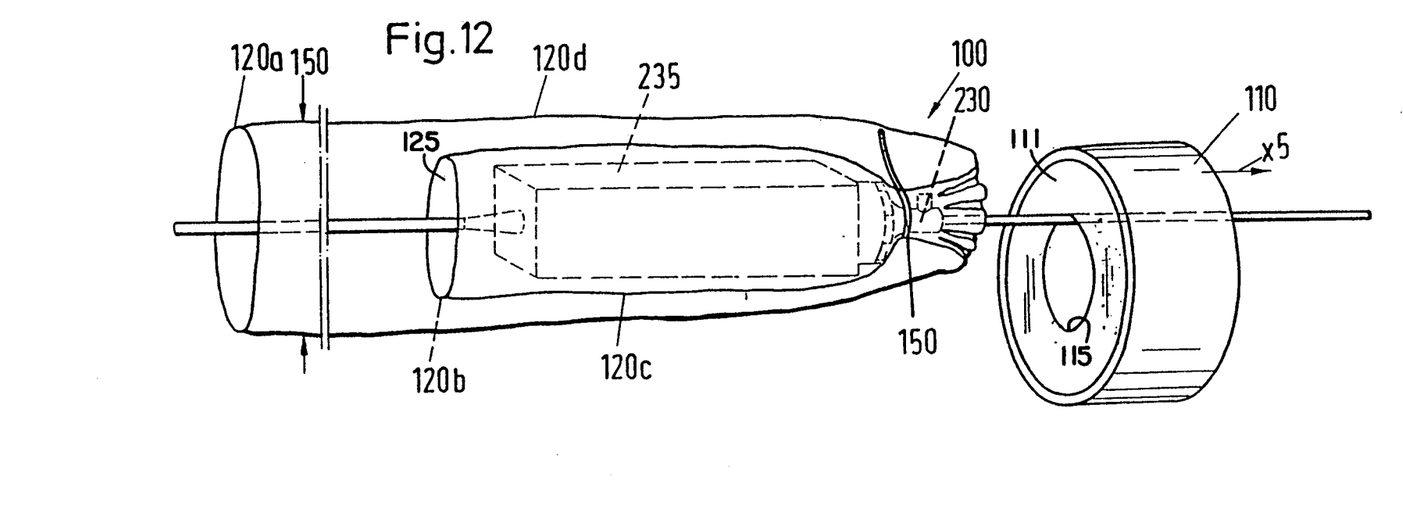
FIG. 12 shows, in a diagrammatical view, the disposable cover with the supply of tubular film disposed within a storage container with the camera doubly enveloped in tubular film and with a laterally removed container.

When the non-sterile camera 235 is introduced into the inner space 125 of the longer, internal tubular film section 120c and mounted onto the arthroscope as shown in FIG. 10, the short, external tubular film section 120d is pulled out from the container 110 thus using up the entire supply of material which is provided by the folded layers 132 thru 137, to be more precise, as far as beyond the tubular film section 128 enveloping the camera 235 as shown in FIG. 11. Following the complete unfolding of the tubular film 120 and thus after the complete consumption of the supply of tubular film 130, the empty container 110 remains behind and the camera 235 with the arthroscope 230 is wrapped twice in film (FIG. 12). The open end of the tubular film section 120d that is drawn over the tubular film section 120c is then sealed by means of a tube clamp. The empty container 110 is pulled off in the direction of the arrow X5 and is not made use of again. The container 110 may be provided with a separating perforation in order to enable one to effortlessly open the container and remove it from the arthroscope 230.

The container 110 consists of pasteboard, cardboard or some other suitable material.

What is claimed is:

1. A disposable cover fabricated from an elongate tubular film for arthroscopy cameras, characterized in that said cover comprises a tubular film supply including a plurality of contiguous film sections folded onto each other and defining a package of folded layers extending transversely of the direction of longitudinal extend of the tubular film and having two end sections defining the terminal ends of said tubular film, one of said end sections extending into and through the other of said end sections, said terminal ends being disposed at the same side of said package.

2. The disposable cover according to claim 1 further characterized in that said one end section extends in the direction of extent of said other end section.

3. A method for covering an arthroscopy camera comprising the steps of providing a disposable sterile cover fabricated from a tubular film, folding contiguous sections of the tubular film onto each other to define a film supply including a package of folded layers having two end sections defining the open terminal ends of the tubular film, moving the end sections relative to each other to extend one of the end sections through and outwardly beyond the terminal end of the other of the end sections, positioning the terminal end of the said one end section in outwardly spaced relation to the terminal end of the other end section, inserting an arthroscope having an optical system into the one end section in the direction of the terminal end thereof, tying off the one end section within the region of the optical system of the arthroscope and in inwardly spaced relation to the terminal end of the one end section, inserting a camera into the one end section through the open terminal end thereof to dispose the camera within the one end section, mounting the camera on the optical system of the arthroscope and within the one end section, pulling the other end section outwardly over the one end section and outwardly beyond the terminal end of the one end section to unfold the film package, turning the portion of the tubular film adjacent the tied off part of the one end section inside out around the optical system of the arthroscope to envelop the one end section and form a two layer film cover for the camera, and tying off the other end section outwardly of the camera.

4. The method for covering an arthroscopy camera according to claim 3 further characterized in that the package of folded layers is disposed within a container having opposing end walls with openings therethrough and said end sections extend outwardly through one of said openings and wherein the step of folding is further characterized as folding successive contiguous sections of said tubular film in concertina-like fashion and the step of moving the end sections is further characterized as inserting one of the end sections into and through and outwardly beyond the other of the end sections.

5. The method of cover an arthroscope camera according to claim 3 wherein the step of folding is further characterized as folding contiguous sections of the tubular film in directions parallel to the direction of longitudinal extent of said tubular film.

6. The method for covering an arthroscope camera according to claim 3 wherein the step of folding is further characterized as folding successive contiguous sections in concertina-like fashion.

7. A disposable cover assembly for an arthroscopy camera, comprising a cover fabricated from a tubular film and including a plurality of contiguous film sections folded onto each other and defining a film supply package of folded layers having two end sections defining the terminal ends of said tubular film, one of said end sections extending into and through the other of said end sections, said terminal ends being disposed at the same side of said package, and a container including opposing end walls having openings therethrough in aligned relation to each other and containing said package, said one end section and said other end section extending outwardly through one of said openings, said one end section extending outwardly beyond the terminal end of said other end section, said film sections being folded to permit said film supply to be pulled out of said container by pulling said other end section over said one end section and outwardly away from said one end section.

8. A disposable cover assembly for an arthroscopy camera, comprising a cover fabricated from a tubular film and including a plurality of contiguous film sections folded onto each other and defining film supply package of folded layers having two end sections defining the terminal ends of said tubular film, one of said end sections extending into and through the other of said end sections, said terminal ends being disposed at the same side of said package, and a container including opposing end walls and containing said package, perforation means for defining openings through said end walls in aligned relation to each other, said film sections being folded to permit said film supply to be pulled out of said container by pulling said other end section over said one end section and outwardly through one of said openings defined by said perforation means and away from said one end section.

9. The disposable assembly cover according to claim 8 further characterized by clamping means for tying-off said one end section.

10. A disposable cover assembly according to claim 8 further characterized in that said folded layers extend in parallel relation to the direction of longitudinal extent of the tubular film.

11. A disposable cover assembly according to claim 8 further characterized in that said folded layers extend transversely of the direction of longitudinal extent of the tubular film.

12. The disposable cover assembly according to claim 8 further characterized in that said package includes at least four folded layers.

13. The disposable cover assembly according to claim 8 further characterized in that said openings comprise circular openings and said tubular film has a cross sectional diameter larger than the diameters of said openings.

14. The disposable cover assembly according to claim 13 wherein said tubular film sections are folded in concertina-like fashion.

* * * * *